United States Patent [19]

Pohndorf

[11] Patent Number: 4,683,895

[45] Date of Patent: Aug. 4, 1987

[54] SUTURE SLEEVE ANCHORING DEVICE

[75] Inventor: Peter J. Pohndorf, Miami, Fla.

[73] Assignee: Cordis Corporation, Miami, Fla.

[21] Appl. No.: 758,741

[22] Filed: Jul. 25, 1985

[51] Int. Cl.[4] .................. A61B 17/04; F16B 15/00
[52] U.S. Cl. .................................... 128/784; 248/71;
248/74.2; 248/505; 604/174
[58] Field of Search ............ 24/20 R, 20 CW, 20 EE,
24/20 S, 23 EE, 457, 458, 459, 483, 484, 485,
523, 522, 531, 533, 575; 128/334 R, 335, 784,
786, DIG. 26, 419 P; 248/71, 74.1, 354;
604/174, 179

[56] References Cited

U.S. PATENT DOCUMENTS

| | | | |
|---|---|---|---|
| 396,677 | 1/1889 | Zimmerman | 248/71 |
| 800,170 | 9/1905 | Potter | 248/71 |
| 3,583,663 | 6/1971 | Snow | 248/71 |
| 4,516,584 | 5/1985 | Garcia | 128/786 |

Primary Examiner—Richard C. Pinkham
Assistant Examiner—Gary Jackson
Attorney, Agent, or Firm—Henry W. Collins; Thomas R. Vigil

[57] ABSTRACT

The anchoring device is used to grip and anchor a suture sleeve received around a pacing lead body to underlying tissue. The anchoring device comprises a unitary body having an upper clip formation adapted to be received around a suture sleeve and a lower staple formation having opposed prongs. When the clip formation is closed about a suture sleeve to grasp the suture sleeve to cause the sleeve to grasp a pacing lead body therein, the prongs will pierce and grasp underlying tissue.

8 Claims, 4 Drawing Figures

SUTURE SLEEVE ANCHORING DEVICE

BACKGROUND OF THE INVENTION

1. Field of the Invention

The present invention relates to a device for use in anchoring a suture sleeve, which is positioned along a pacing lead body, to underlying tissue. More specifically, the invention relates to a device similar to function to a staple, which can be used in place of a suture for securing a suture sleeve in place.

2. Description of the Prior Art

Heretofore, in the implantation of a pacing lead in an atrium or ventricle of a heart, a surgeon makes an incision at the venous site of choice. Next, a pacing lead, with an elastomeric suture sleeve thereon, is inserted into the right or left cephalic vein or the right external jugular vein.

Then, a tip electrode of the lead is moved through the vein and into an atrium or ventricle of the heart and fixed in place.

After determining that the electrode position is satisfactory, the lead is connected to a pacer unit to be implanted within a pocket in the body.

Next, the suture sleeve, which is movable on the lead, is moved along the lead to a location where it is desired to fasten the lead to underlying tissue.

Typically such suture sleeve is provided with at least two spaced apart circumferential grooves, each for receiving a suture therein. A suture is passed through the underlying tissue and tied within one of the grooves to secure the suture sleeve and pacing lead therein in place and this procedure is repeated with another suture which is secured in the other groove.

Placement of sutures is time consuming and if not placed properly, slippage of the suture sleeve from the grasp of the sutures could occur, thus leading to displacement of the tip of the pacing lead.

The anchoring device of the present invention differs from a suture and comprises a body having an upper partially circular clip formation and a lower staple formation including opposed prongs which, when the clip formation is fitted around a suture sleeve in a suture receiving groove thereof, pierce and grip tissue in a pincer movement to fix the anchoring device to the tissue while the upper circular clip formation grips the suture sleeve.

SUMMARY OF THE INVENTION

According to the present invention there is provided an anchoring device for gripping and anchoring a suture sleeve received around a pacing lead body to underlying tissue, said anchoring device comprising: a unitary body having an upper clip formation adapted to be received around a suture sleeve and a lower staple formation having opposed prongs which, when said clip formation is closed about a suture sleeve to grasp the suture sleeve to cause the sleeve to grasp a pacing lead body therein, will pierce and grasp underlying tissue.

Further according to the invention there is provided a method for anchoring a suture sleeve using the anchoring device described above, said method comprising the steps of: positioning a cardiac pacing lead at a desired location within a heart; sliding a suture sleeve upon the body of the lead to a position where it is to be secured to underlying tissue; placing said anchoring device over the suture sleeve; and, causing the device to close about the suture sleeve to cause said upper clip formation to grasp the suture sleeve to cause same to grasp the lead body and at the same time to cause said prongs to pierce and grasp tissue underlying the suture sleeve.

DESCRIPTION OF THE PREFERRED EMBODIMENT

Figure 1:
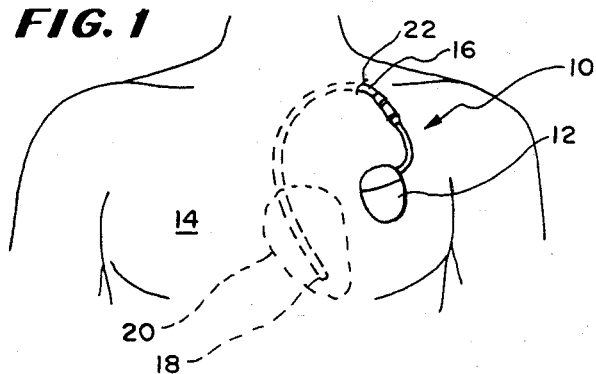
FIG. 1 is a front elevational view of a human upper torso of a patient and shows a pacing lead extending between a pacer and a heart with the lead being fixed by a suture sleeve and anchoring devices of the present invention to the patient's skin.

Referring now to FIG. 1 in greater detail, there is illustrated therein a pacer system 10 including a pacer 12 adapted to be inserted in a pocket on the chest 14 of a patient and a pacing lead 16 having a tip electrode assembly 18 implanted within the patient's heart 20. The pacing lead 16 extends from the pacer 12 to a position or area 22 where the pacing lead 16 extends into and through a vein to the heart 20 where the tip electrode assembly 18 is positioned in a chamber of the heart 20 for pacing of the heart 20.

Once the tip electrode assembly 18 of the pacing lead 16 is appropriately positioned, an elastomeric suture sleeve 24, which has been positioned on the lead 16 and which is movable thereon, is moved along the lead 16 to a location where it is desirable to fasten the lead 16 to underlying tissue. In FIG. 1, the suture sleeve 24 is fastened to underlying tissue in the area 22 where the pacing lead 16 exits the vein.

Figure 2:
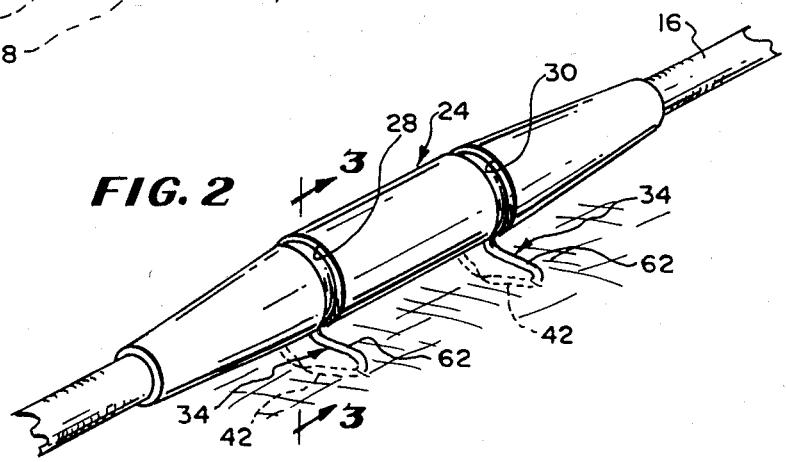
FIG. 2 is a perspective view of a suture sleeve with two anchoring devices positioned within respective suture receiving grooves of the suture sleeve for anchoring the suture sleeve to underlying tissue.

Referring now to FIG. 2, there is illustrated therein an enlarged view of the suture sleeve 24 shown in FIG. 1. As shown, the suture sleeve 24 has a lumen 26 through which the pacing lead 16 extends and has two spaced apart suture receiving grooves 28 and 30 which extend circumferentially about the suture sleeve 24. Typically, in conventional use of the suture sleeve 24, sutures (not shown) are tied around and in the suture grooves 28 and 30 and sewn through underlying tissue to secure the sleeve 24 with a pacing lead body therein to the underlying tissue.

This procedure is time consuming and, if such sutures are not properly secured in place, the suture sleeve 24 may slip free of the sutures and cause movement of the pacing lead 16.

To eliminate the possibility of slippage of the suture sleeve 24 and the time consuming operation of suture placement, the suture sleeve 24 is secured in place with anchoring devices 34 constructed according to the teachings of the present invention.

Figure 3:
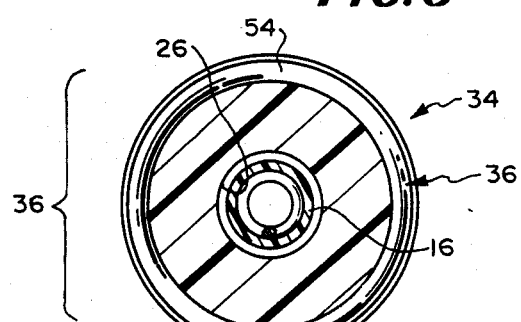
FIG. 3 is a sectional view of the suture sleeve shown in FIG. 2, is taken along line 3—3 of FIG. 2 and shows the position of one anchoring device within a suture groove in the suture sleeve and fixed in underlying tissue.

As shown in FIG. 3, each anchoring device 34 is in the form of a staple-like clip 34 and comprises an upper partially circular clip formation 36 which is received around and squeezed into a suture groove 28 or 30 and a lower staple formation 38 comprising prongs 41 and 42 which pierce underlying tissue to fix the suture sleeve 24 in place when the clip formation 36 is squeezed about a suture sleeve 24 juxtapositioned to skin or tissue.

The suture sleeve anchoring device 34 of the present invention is sized and configured so that the clip formation 36 easily fits into a suture receiving groove 28 or 30 for securely grasping the suture sleeve 24 which in turn grasps the lead 16 therein while the prongs 41 and 42 of the staple formation 38 pierce and grasp tissue underlying the suture sleeve 24.

Figure 4:
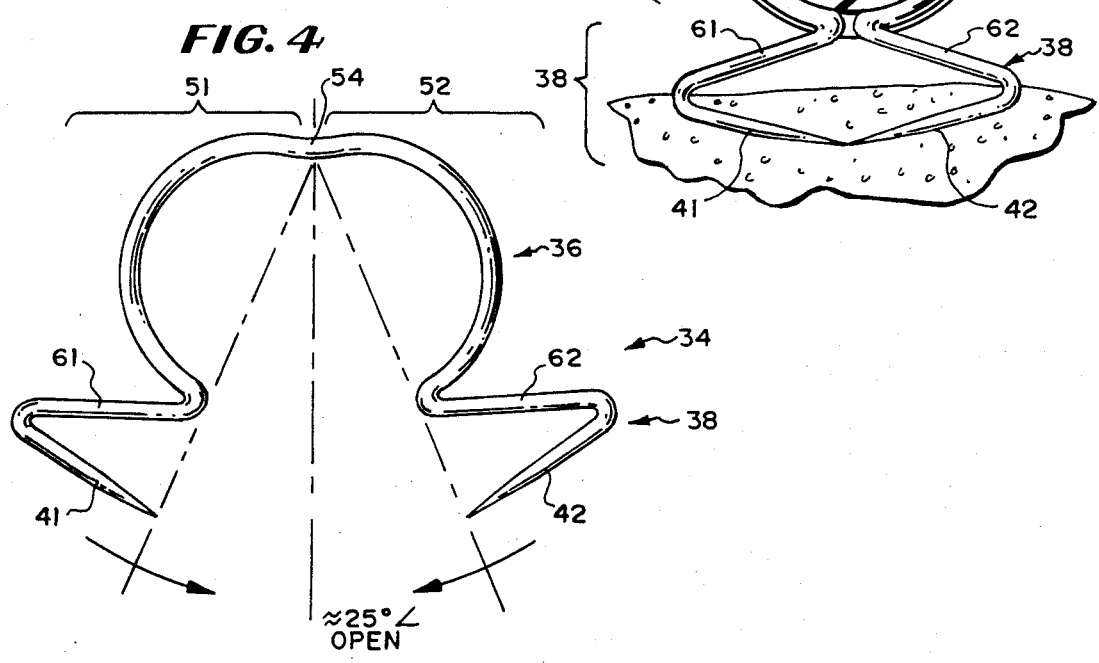
FIG. 4 is a plan view of the anchoring device of the present invention and shows the anchoring device in an open position thereof.

Turning now to FIG. 4, there is illustrated therein one suture sleeve anchoring device 34 of the present invention. Typically, the anchoring device 34 is made of 0.080 diameter soft annealed 316L stainless steel, for purposes of flexibility as well as for purposes of sterilizability.

The device 34 is shown in FIG. 4 in an open position and opposite sides thereof form two mirror image sections 51 and 52 which are connected, i.e., integral, at a point 54 in the clip formation 36. The sections 51 and 52 when closed together (FIG. 3) have the shape of a lopsided FIG. 8. The lower staple formation 38 forming the bottom portion of the FIG. 8 is shallower and broader than the upper circular clip formation 36 forming the upper portion of the FIG. 8.

The staple formation 38 includes, in each mirror image section 51,52, a laterally outwardly extending arm 61 or 62 which is integral, at its outer end, with one of the inwardly extending prongs 41,42 and integral, at its inner end, with the clip formation 36.

In use, as shown in FIGS. 2 and 3, once a pacing lead 16 with a suture sleeve 24 received thereon has been properly positioned, each anchoring device 34 is activated (squeezed) to cause the suture sleeve 24 to grasp the body of the lead 16 extending through the lumen 26 thereof.

In other words, each anchoring device 34 is positioned about the suture sleeve with the clip formation 36 received in one of the grooves 28 or 30. Once positioned in this manner, the two mirror image sections 51 and 52 are flexed toward each other until the prongs 41 and 42 are forced into the underlying tissue and the clip formation 36 firmly grasps the suture sleeve 24 in the area of one of the suture grooves 28 or 30.

To facilitate grasping of underlying tissue, each prong 41,42 extends from an arm 61 or 62 inwardly and downwardly toward an opposed prong 42 and 41.

Preferably the partially circular clip formation 36 of the FIG. 8 is provided with a diameter which is slightly smaller than the diameter of the suture sleeve 24 at the bottom of the suture groove 41 or 42 so that the diameter of the suture sleeve 34 at the bottom of the suture groove 28 or 30 is compressed inwardly upon placement of the anchoring device 34 to ensure a good compressive grasp of the sleeve 24 by the device 34.

In removing each anchoring device 34, the procedure is reversed in that each anchoring device 34 is opened by moving the mirror image sections 51 and 52 away from each other to release the prongs 41,42 from the underlying tissue and the clip formation 36 from the suture sleeve 24.

From the foregoing description it will be apparent that the anchoring device 34 of the present invention has a number of advantages some of which have been described above and others of which are inherent in the invention. For example, once squeezed into place, the device 34 will not slip from its position around the suture sleeve 24 as sometimes occurs with sutures. Further, because of the ease of insertion and removal of the device 34, time, typically required to correctly place and tie sutures, is saved.

Also, modifications can be made to the anchoring device 34 of the present invention without departing from the teachings of the present invention. For example, the device 34 can be made of a spring metal and initially held apart by a plug (not shown) positioned between the mirror image sections 51,52 in the area of the junction between the clip formation 36 and the staple formation 38 in each section 51,52 beneath a suture sleeve 24. Such a modified device 34 is set by removing the plug to allow the prongs 41,42 to move toward each other into underlying tissue. Removal of such a spring metal anchoring device 34 is the same as for a non-spring metal anchoring device 34.

Accordingly, the scope of the invention is only to be limited as necessitated by the accompanying claims.

We claim:

1. An anchoring assembly for affixing a lead body to tissue, said anchoring assembly comprising:
   a biocompatible suture sleeve having a tube wall defining an axial orifice, the tube wall including at least one external circumferential groove and surrounding the lead body which extends axially through the orifice; and
   a biocompatible anchoring device compressively manipulatable with hand tools from an open position to an affixed position, said anchoring device including: a first generally hemicircular portion adapted to be received within the side of a circumferential groove of said biocompatible suture sleeve; a second generally hemicircular portion adapted to be received within the other side of said circumferential groove of said biocompatible suture sleeve; a moderately stiff hinge means portion extending between said first and second generally hemispherical portions which is deformed by manipulation to cause said device to move from the open position to the affixed position; a first staple portion depending from said first generally hemicircular portion at and end of said first generally hemicircular portion farthest from said hinge portion and including a prong outwardly offset from the arc of said hemicircular portion in a manner which is adapted to puncture and then grip tissue as said device is manipulated from the open to the affixed position; and a second staple portion depending from said generally hemicircular portion at an end of said second generally hemicircular portion farthest from said hinge portion and including a prong outwardly offset from the arc of said hemicircular portion in a manner which is adapted to puncture and then grip tissue as said device is manipulated from the open to the affixed position.

2. The anchoring device of claim 1 wherein said body is made of stainless steel.

3. The anchoring device of claim 2 wherein said stainless steel is soft, annealed 316L stainless steel.

4. The anchoring device of claim 1 wherein said body is made of stainless steel wire having a diameter of approximately 0.020 inch.

5. The anchoring device of claim 1 wherein the partially circular clip formation of the device has a diameter which is less than the diameter of the suture sleeve at the bottom of the suture receiving groove to provide compression of the suture sleeve around the lead body.

6. The anchoring device of claim 1 wherein said clip formation and said staple formation include laterally opposed mirror image side sections.

7. The anchoring device of claim 6 wherein said staple formation includes, in each mirror image section, a laterally outwardly extending arm which extends between said clip formation and an outer end of one of said prongs.

8. The anchoring device of claim 7 wherein each prong extends inwardly of the device and downwardly from one of said arms toward the opposed prong.

* * * * *